United States Patent
Evans et al.

(10) Patent No.: US 6,508,782 B1
(45) Date of Patent: Jan. 21, 2003

(54) THROMBOLYSIS DEVICE

(75) Inventors: Michael Evans, Palo Alto, CA (US); Will R. Dubrul, Redwood City, CA (US)

(73) Assignee: Bacchus Vascular, Inc., Santa Clara, CA (US)

( * ) Notice: Subject to any disclaimer, the term of this patent is extended or adjusted under 35 U.S.C. 154(b) by 85 days.

(21) Appl. No.: 09/640,499

(22) Filed: Aug. 16, 2000

Related U.S. Application Data

(63) Continuation of application No. 09/504,162, filed on Feb. 15, 2000, which is a continuation of application No. 09/005,217, filed on Jan. 9, 1998, now Pat. No. 6,287,271, which is a continuation-in-part of application No. 08/483,071, filed on Jun. 7, 1995, now Pat. No. 5,713,848, which is a continuation-in-part of application No. 08/320,184, filed on Oct. 7, 1994, now Pat. No. 5,498,236, which is a continuation of application No. 08/065,470, filed on May 19, 1993, now Pat. No. 5,380,273, which is a continuation-in-part of application No. 07/885,665, filed on May 19, 1992, now abandoned.

(51) Int. Cl.[7] .............................................. A61B 17/20
(52) U.S. Cl. ........................ 604/22; 604/20; 604/96.01; 604/101.01
(58) Field of Search .............................. 604/22, 20, 49, 604/96.01, 101.05, 101.01; 606/169, 170, 171; 601/2

(56) References Cited

U.S. PATENT DOCUMENTS

| | | |
|---|---|---|
| 3,352,303 A | 11/1967 | Delaney |
| 3,565,062 A | 2/1971 | Kuris |
| 3,809,093 A | 5/1974 | Abraham |
| 3,823,717 A | 7/1974 | Pohlman et al. |
| 3,828,770 A | 8/1974 | Kuris et al. |
| 3,861,391 A | 1/1975 | Antonevich et al. |
| 3,996,938 A | 12/1976 | Clark, III et al. |
| 4,404,971 A | 9/1983 | LeVeen et al. |
| 4,445,892 A | 5/1984 | Hussein et al. |
| 4,636,195 A | 1/1987 | Wolinsky |
| 4,692,139 A | 9/1987 | Stiles |
| 4,705,502 A | 11/1987 | Patel |

(List continued on next page.)

FOREIGN PATENT DOCUMENTS

| | | |
|---|---|---|
| WO | WO 98/38929 | 9/1998 |
| WO | WO 99/16362 | 4/1999 |
| WO | WO 00/03651 | 1/2000 |

*Primary Examiner*—Teresa Walberg
*Assistant Examiner*—Fadi H. Dahbour
(74) *Attorney, Agent, or Firm*—Townsend and Townsend and Crew LLP

(57) ABSTRACT

The present invention describes a catheter suitable for introduction into a tubular tissue for dissolving blockages in such tissue. The catheter is particularly useful for removing thrombi within blood vessels. In accordance with the preferred embodiments, a combination of vibrating motion and injection of a lysing agent is utilized to break up blockages in vessels. The vessels may be veins, arteries, ducts, intestines, or any lumen within the body that may become blocked from the material that flows through it. As a particular example, dissolution of vascular thrombi facilitated by advancing a catheter through the occluded vessel, the catheter causing a vibrating, stirring action in and around the thrombus usually in combination with the dispensing of a thrombolytic agent such as urokinase into the thrombus. The catheter has an inflatable or expandable member near the distal tip which, when inflated or expanded, prevents the passage of dislodged thrombus around the catheter. The dislodged portions of thrombus are directed through a perfusion channel in the catheter, where they are removed by filtration means housed within the perfusion channel before the blood exists the tip of the catheter. Catheters that allow both low frequency (1–100 Hz) vibratory motion and delivery of such agents to a blockage and a method for using such catheters are disclosed.

46 Claims, 9 Drawing Sheets

U.S. PATENT DOCUMENTS

| | | |
|---|---|---|
| 4,735,604 A | 4/1988 | Watmough et al. |
| 4,781,677 A | 11/1988 | Wilcox |
| 4,808,153 A | 2/1989 | Parisi |
| 4,815,478 A | 3/1989 | Buchbinder et al. |
| 4,824,436 A | 4/1989 | Wolinsky |
| 4,834,703 A | 5/1989 | Dubrul et al. |
| 4,867,141 A | 9/1989 | Nakada et al. |
| 4,870,953 A | 10/1989 | Don Micheal et al. |
| 4,898,575 A | 2/1990 | Fischell et al. |
| 4,911,163 A | 3/1990 | Fina |
| 4,920,954 A | 5/1990 | Alliger et al. |
| 5,058,570 A | 10/1991 | Idemoto et al. |
| 5,069,664 A | 12/1991 | Guess et al. |
| 5,090,960 A | 2/1992 | Don Michael |
| 5,163,421 A | 11/1992 | Bernstein et al. |
| 5,163,905 A | 11/1992 | Don Michael |
| 5,176,638 A | 1/1993 | Don Michael |
| 5,195,955 A | 3/1993 | Don Michael |
| 5,222,941 A | 6/1993 | Don Michael |
| 5,243,997 A | 9/1993 | Uflacker et al. |
| 5,248,296 A | 9/1993 | Alliger |
| 5,304,115 A * | 4/1994 | Pflueger et al. ............... 604/22 |
| 5,328,470 A | 7/1994 | Nabel et al. |
| 5,342,306 A | 8/1994 | Don Michael |
| 5,380,273 A | 1/1995 | Dubrul et al. |
| 5,380,284 A | 1/1995 | Don Michael |
| 5,460,610 A | 10/1995 | Don Michael |
| 5,462,529 A | 10/1995 | Simpson et al. |
| 5,716,340 A * | 2/1998 | Schweich, Jr. et al. . 604/101.05 |
| 5,725,535 A * | 3/1998 | Hedge et al. .......... 604/101.01 |
| 5,833,644 A | 11/1998 | Zadno-Azizi et al. |
| 5,836,905 A | 11/1998 | Lemelson et al. |
| 5,951,514 A * | 9/1999 | Sahota ................. 604/101.05 |
| 5,968,069 A * | 10/1999 | Dusbabek et al. ....... 604/96.01 |
| 6,099,497 A * | 8/2000 | Adams et al. ........... 604/96.01 |

* cited by examiner

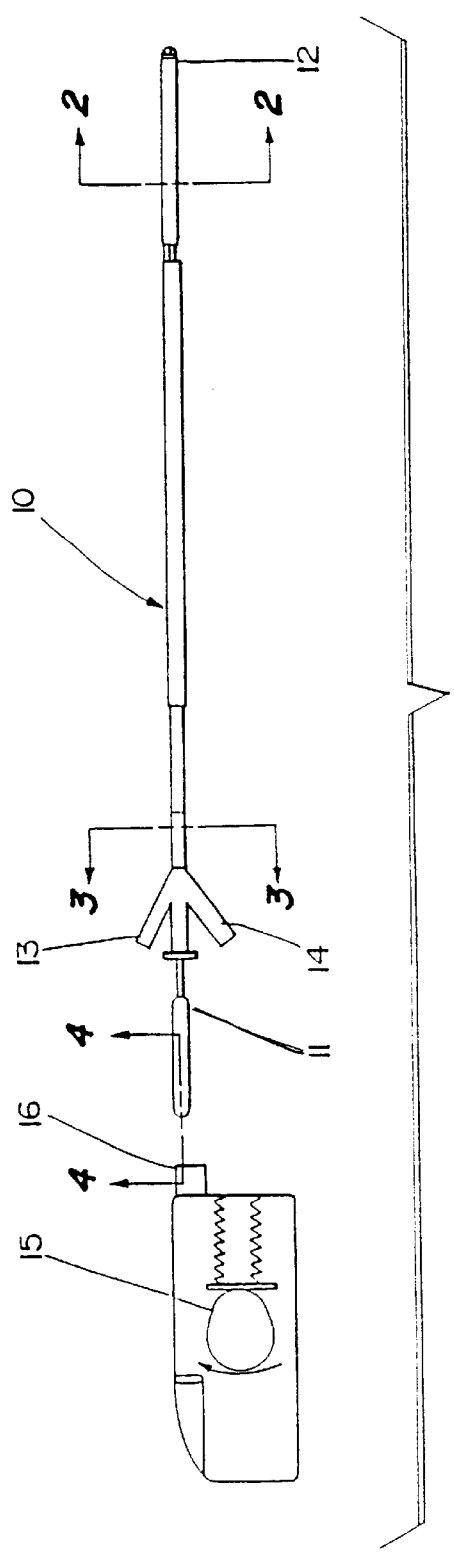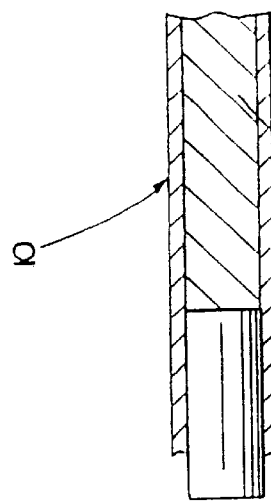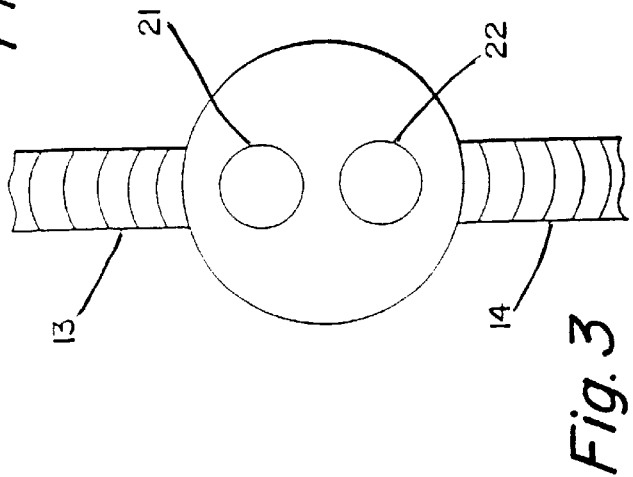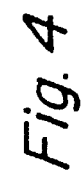

THROMBOLYSIS DEVICE

CROSS-REFERENCES TO RELATED APPLICATIONS

The present application is a continuation of Ser. No. 09/504,162, filed on Feb. 15, 2000, which was a continuation of application Ser. No. 09/005,217, filed on Jan. 9, 1998, now U.S. Pat. No. 6,287,271, which was a continuation-in-part of application Ser. No. 08/483,071, filed on Jun. 7, 1995, now U.S. Pat. No. 5,713,848, which was a continuation-in-part of application Ser. No. 08/320,184, filed on Oct. 7, 1994, now U.S. Pat. No. 5,498,236, which was a continuation of application Ser. No. 08/065,470, filed on May 19, 1993, now U.S. Pat. No. 5,380,273, which was a continuation-in-part of application Ser. No. 07/885,665, filed on May 19, 1992, now abandoned, the full disclosures of which are incorporated herein by reference.

BACKGROUND OF THE INVENTION

1. Field of the Invention

The present invention is generally directed to removal of blockage of tubular tissue and specifically directed to the dissolution of intravascular thrombi.

2. Description of the Background Art

It is well known that the formation of thrombi (clots) in blood vessels is a serious medical malady. Thrombi are correlated to the formation of plaque buildup in blood vessels and when blockage occurs, it is more a result of the thrombi than of the plaque buildup (which is usually referred to as atherosclerosis when it is involved in arteries).

All thrombi need not be treated interventionally, but in many instances thrombi do, in fact, become life threatening and require removal or at least reduction in size. A thrombus is primarily comprised of red blood cells and fibrin. There are several treatments which could be adapted for the removal of thrombi in vessels which involve intravascular catheters. Most such intravascular catheters have been designed primarily for plaque removal and contain an element that vibrates at ultrasonic frequencies. Representative of such atherectomy catheters are U.S. Pat. Nos. 5,069,664, 4,920,954, 4,898,575, and 4,808,153. Some involve cutting the plaque off of the wall of the vessel using a cutting blade. Some may be adapted to facilitate removal of a thrombus in a vessel. For example, DonMichael, et al., in U.S. Pat. No. 4,870,953, describes an intravascular catheter having a bulbous head at its distal end which vibrates at ultrasonic frequencies. It is suggested that such a tip might be useful for disintegrating a thrombus. DonMichael, et al., also teaches the discharge of a radiographic contrast medium from the catheter tip to enable visualization of the cleared vessel. A second cooling solution may be circulated through the catheter to the tip to prevent overheating of the bulbous tip. All the foregoing intravenous catheters have their shortcomings. None are particularly adapted for removing thrombi.

The use of laser catheters for treatment of thrombi is not uncommon, and significant damage to vessels during this treatment have been reported. The use of drugs for the primary dissolution of these clots is extremely common and is often considered the primary treatment of choice when a thrombus is present. These drugs are referred to as thrombolytic agents (meaning clot dissolution or decomposition). The most common thrombolytic agents (drugs) that are used presently in the treatment of vascular thrombosis are such agents as urokinase, streptokinase, TPA, leech saliva and other such pharmaceutical clot dissolving agents. Significant problems such as hemorrhagic complications, early rethrombosis, prolonged infusion times, costs, significant failure rates, etc., are persistent problems with the use of these pharmaceutical agents. To overcome the aforesaid problems with drugs, an intravascular spraying catheter may be placed in or near a thrombus and the clot periodically sprayed (or pulsed) with a thrombolytic agent which facilitates clot dissolution. Using intermittent spraying of thrombolytic agents may enable the use of less drug over a shorter time period to effect for thrombolysis when compared to the more classical approach of allowing the drug to drip in or near the clot. But even this approach requires excessive time and drug amount. In addition, the use of pulsatile injections of thrombolytic agents may result in pieces of the clot fracturing off from the main body of the clot and causing an embolism which is a danger faced by interventionalists performing this procedure. It is, therefore, desirable to provide an improved catheter for delivering thrombolytic agents which reduce the time and amount of pharmaceutical agent required for thrombolysis and which reduces the danger of embolism.

Stiles, in U.S. Pat. No. 4,692,139 (incorporated herein by reference), describes a catheter for removing obstructions from biological ducts which transmits ultrasonic vibrations to the obstruction to facilitate lysis. Stiles' catheter has means for administering a lysing agent and simultaneously administering ultrasonic vibrations to obstructing material forward of the catheter tip. The Stiles catheter has a vibrating probe which probe (when the catheter is deployed within a vessel) projects from the tip of the catheter. There is no teaching of any advantages to be gained by either (a) vibrating the catheter (as opposed to a probe housed within a catheter), or (b) using low frequencies (frequencies below 1000 Hz). Further, Stiles teaches the use of vibrational frequencies in the range "of at least 60 KHz." The vibrational frequency employed to effect lysis is an important issue. It is noted that at the frequencies suggested by Stiles' teaching, the wavelength of ultrasound in the probe is $$\lambda = \frac{v}{f} < \frac{1000}{f} < \frac{1000}{60,000}$$

or $\lambda < 1/60$ foot. Thus, in Stiles' catheter there are normally many wavelengths of ultrasound between the ultrasonic source and the probe tip. Wherever the probe tip touches the surrounding aspiration tube walls and/or aspirate, energy will be lost due to heating. Thus, it is difficult or impossible to control the amount of ultrasonic vibratory energy reaching the tip of the probe. Depending on the amount of loss of ultrasonic vibrational energy that occurs along the length of the probe (which, of course, depends on the amount of aspirate in the aspirator tube and the amount of mechanical contact between the probe and the surrounding walls) the energy actually delivered to tissue at the probe tip may either ablate or weld tissue, emulsify an obstruction or be insufficient to have any effect on an obstruction.

Lower frequency vibrations (less than 100 Hz) have wavelengths greater than one foot. The amplitude and, therefore, the energy of the low frequency vibration delivered to the tip of a catheter is much more predictable at the lower frequencies and enable more accurate dosimetry. This is because the vibratory loss to surrounding tissue is due to uniform frictional losses along the length of the elongate member (inserted catheter). Stiles' probe, which vibrates at ultrasonic frequencies as noted above, is housed within an aspiration tube where it may unpredictably be loaded by contact with any aspirate that may be present or the surrounding catheter walls. That is, the undesirable coupling of vibratory energy out of the Stiles' probe is unpredictable. It would be desirable to provide an interventional catheter having a structure wherein the vibrating element contacts the tissue along its entire length.

All of the prior art thrombolysis catheters have specified ultrasonic frequencies (above audible frequencies) when advocating adjunctive vibratory waves to assist thrombolysis. Perhaps this is due to the availability of compact solid state crystals that oscillate or may be driven at these frequencies. Perhaps it is the belief that these frequencies assist in "emulsifying" an obstruction such as a thrombus. Whatever the reason, the present teaching surprisingly shows that the application of low frequency mechanical vibrations facilitate thrombus disintegration. Even more surprisingly, this is true even in the absence of an exogenous lysing agent.

SUMMARY OF THE INVENTION

While the invention is best understood and taught by making reference to the invention in context of a particular application such as the treatment of vascular thrombosis, it is the object of the present invention to provide a catheter (herein alternatively referred to as a "motion catheter" or a "vibrating catheter") that can be placed in a blocked lumen in the body and, by either utilizing the motion of the catheter alone or the catheter motion in combination with the dispensing of a medicament suitable for dissolving such blockage, dislodge or more preferably, dissolve said blockage. This motion catheter, which may be simply a moving wire, can be used alone for blockage removal or with a lysing agent to dissolve the blockage. Most preferably, both motion and dispensing are used in combination to effect blockage removal.

The objects of this invention are achieved, in general, by providing a vibrating wire, or alternatively, a vibrating catheter that has an open lumen for delivery of said lysing agents. The vibrating catheter may have one or more directional channels for delivery of a lysing agent which channel (s) are attached to a pump so that delivery of said lysing agent can be controlled with respect to delivery time and delivery rate of the lysing agent.

Because blockage of lumens in the body are often times visualized with image enhancement devices, the catheter of the present invention is conveniently placed by means of fluoroscopy, ultrasound or the like. The motion catheter may be placed in the body in any tubular tissue in proximity to said blockage so that the motion of the catheter will dislodge or preferably dissolve the blockage.

A specific application of the aforementioned motion catheter is the dissolution of blood clots or thrombi with or without the use of a lysing/thrombolytic agent such as urokinase, streptokinase or a similar lysing agent. If the distal tip of the motion catheter is placed in juxtaposition to a blood clot (proximal, distal, inside or adjacent to the clot), the low frequency (1–5000 Hz) motion of the catheter facilitates the dislodgment by mechanical agitation of the thrombolytic clot. Dissolution may be achieved if the vibrating catheter also dispenses a thrombolytic agent. Usually the thrombi are located in an artery. As a thrombus dissolves, it is desirable that the tip of the motion catheter be moved (with regard to its original placement/location) to keep the tip in juxtaposition with the clot and to further facilitate the dissolution of the thrombi.

BRIEF DESCRIPTION OF THE DRAWINGS

FIG. 1 is a schematic view of a preferred embodiment of the motion catheter of the present invention.

FIG. 2 is a cross-sectional view of the distal treatment tip of the catheter of FIG. 1 along line 2—2.

FIG. 3 is a cross-sectional view of the motion catheter of FIG. 1 taken near the proximal end of the catheter along line 3—3.

FIG. 4 is a longitudinal cross-sectional view of the proximal end of the motion catheter of FIG. 1 taken along line 4—4.

DESCRIPTION OF THE SPECIFIC EMBODIMENTS

Figure 5:
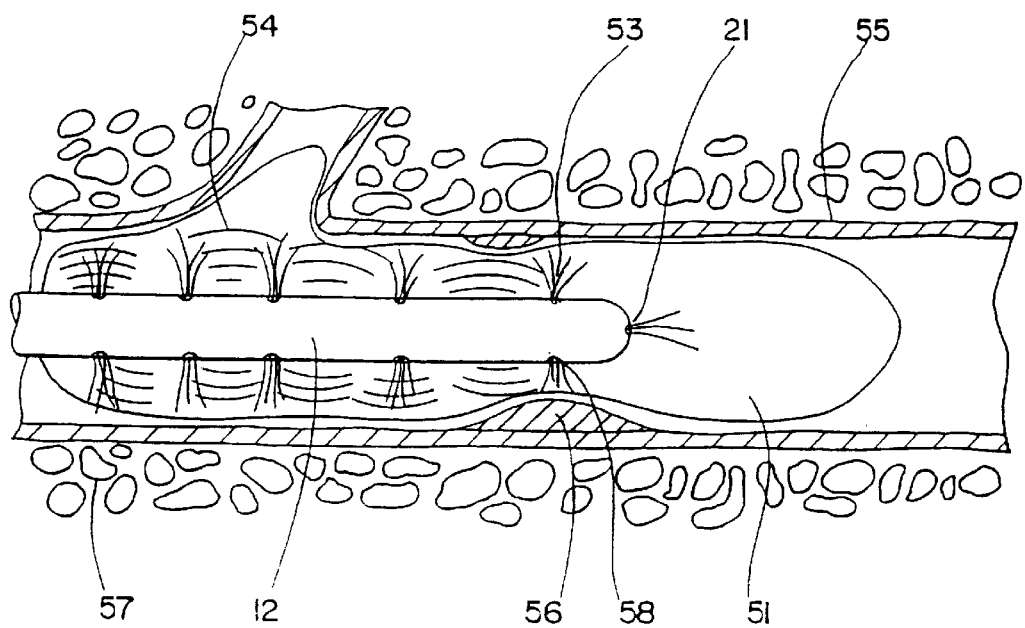
FIG. 5 is a schematic perspective view of the preferred embodiment of the motion catheter of the present invention wherein the distal treatment tip of the catheter of the present invention is embedded in the obstruction (shown in cross-section) causing blockage of the lumen.

Turning now to FIG. 1, a preferred embodiment of the motion catheter of the present invention is generally indicated at the numeral 10. The catheter 10 has a proximal end 11 and a distal or treatment end 12. The proximal end 11 matingly engages a vibrating member 16 which vibrating member 16 is driven by an oscillator 15. The catheter 10 may have one or more lumens extending from the proximal end to the distal end. One lumen, which is optional, is a guidewire lumen which enters the catheter through the guidewire lumen port 13 and exits the catheter through the distal tip 12. A second lumen, having an entry port generally indicated at 14, extends the length of the catheter to the distal tip 12 and is used as a conduit for transporting a lysing agent or other compatible fluid (e.g., saline) from a reservoir (not shown) to the distal tip 12 of the catheter 10.

The distal tip 12 of the catheter 10, which may be radiopaque, is shown in cross-section in FIG. 2. A lysing agent lumen 21 extends the length of the catheter connecting the lysing agent entry port 14 with dispensing holes near the distal tip 12. There may be one or more holes surrounding the tip 12, which holes are in fluid communication with the lysing agent lumen 21. The guidewire lumen 22, which is optional, enables the use of the catheter with a guidewire. The guidewire (not shown) may be introduced into the vessel in which the catheter is to be inserted for removing blockage. The abnormal narrowing or constriction of a passage or lumen such as results from a clot lodged in a blood vessel is called a stenosis. The guidewire is advanced, usually by means of x-ray, until it reaches the point of stenosis. The guidewire may then be either forced through the stenosis or it may terminate at the stenosis. The catheter 10, may then be inserted over the guidewire and advanced so that the distal tip 12 of the catheter is in juxtaposition with the blockage. While for many applications the presence of a guidewire lumen is necessary, for other applications it is not required. A pump (not shown) may be used to force a lysing agent into the lysing agent lumen 21 through the entrance port 14.

It is known in the prior art to be advantageous to have an element within an intravascular catheter capable of vibration at high frequencies. Such catheters normally require the element to vibrate at ultrasonic frequencies to effect the result desired. Accordingly, such catheters employ a titanium wire coupled to an ultrasonic generator such as a piezoelectric crystal which causes the wire to vibrate longitudinally at ultrasonic frequencies. In these instances, the ultrasonic energy is transferred to the medium surrounding the vibrating element and is used to cause cavitation at the tip of the catheter, which cavitation may cause the disruption of the blockage. Alternatively, an ultrasonic transducer may be placed at the tip of the catheter to emit ultrasonic waves laterally therefrom and receive reflections from the walls of the surrounding vessel thereby providing an ultrasonic image of the vessel wall. The use of ultrasonic frequencies produces heat, both along the wall of the catheter and at the tip which requires a cooling fluid. In addition, titanium must be used in order to prevent fracture of the wire.

In the present invention, the entire catheter 10 is coupled to a source of vibrational energy 16 driven by an oscillator 15 operating in the range of 2 to 1000 oscillations per second. These low frequency vibrations transmit along the catheter to its distal tip 12 providing a mechanical motion of the tip. Such mechanical motion can be used to mix a lysing agent with a blockage near the distal tip. The vibrating agent 16 (FIG. 1) is inserted into the proximal end of the motion catheter 10 as shown in greater detail in FIG. 4. The proximal end 11 of the catheter 10 matingly engages the oscillating element 16. The oscillating element 16 reciprocates in the direction of the long axis of the catheter 10. Alternatively, the oscillating element 16 may rotate to-and-fro causing a back and forth rotary motion along the wall of the catheter which is translated to the tip. Or a to-and-fro motion may be used in combination with a back and forth translational motion to effect a wobbling motion at the tip. The use of such motion in combination with the dispensing of a medicament such as a lysing agent at the tip of the catheter is illustrated in FIGS. 5 through 10.

In FIG. 5, the distal tip 12 of catheter 10 is shown advanced into a blood vessel 55. The blood vessel inner wall 55 is surrounded by tissue generally indicated by 57. An obstruction 51 in the vessel is penetrated by the distal treatment tip 12 of the catheter 10. Once tip 12 of the catheter 10 is within the obstruction 51 (such as a blood clot) a lysing agent 53 is dispensed from the holes 58 near the tip of the catheter by means of pumping the lysing agent 53 from a reservoir (not shown) through the lysing agent lumen 21. At the same time, the mechanical motion of the tip, generally indicated at 54, is induced in the distal tip of the catheter by means the vibrating element 16. The combination of lysing agent 53 emanating from holes 58 in the distal tip 12 of the catheter 10 in combination with the vibratory motion 54 of the distal tip of the catheter assists in the penetration of the lysing agent into the obstruction 51, and provides an advantage over prior art.

Figure 6:
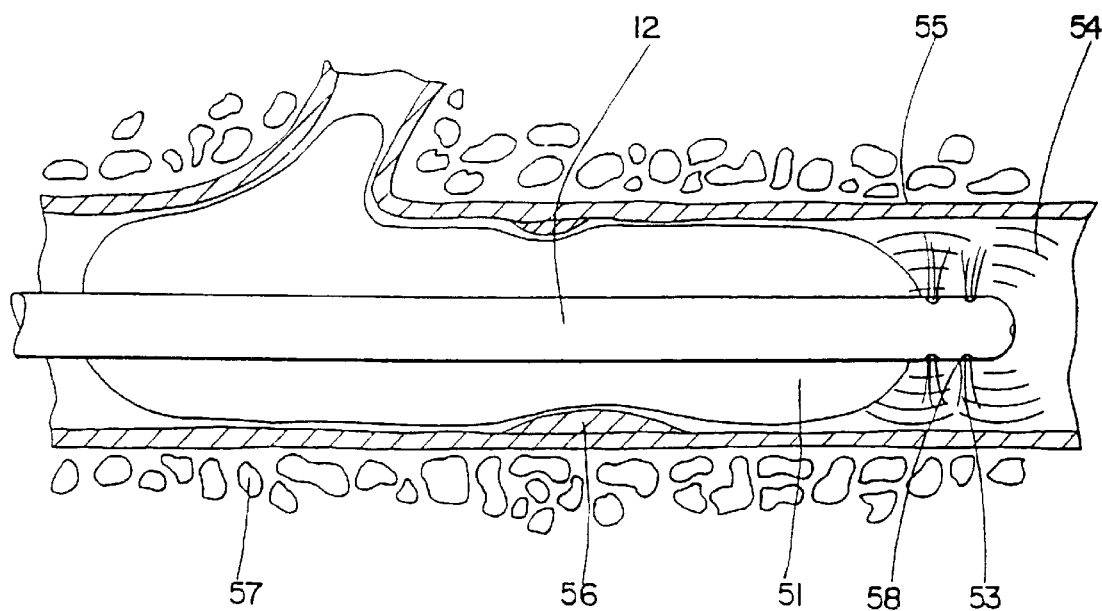
FIG. 6 is a schematic perspective of the preferred embodiment of the present invention shown in FIG. 5 wherein the motion catheter passes through or around the obstruction and the lysing agent (if required) emanates from the most distal portion of the catheter.

Alternatively, the distal tip 12 of the catheter 10 may be inserted into the blockage 51 and passed completely therethrough, as shown in FIG. 6, so that the very distal-most portion of the distal tip 12 extends beyond the obstruction 51. In such an event, motional waves 54 may be used in combination with the release of a lysing agent 53 from holes 58 in the distal tip to facilitate dissolution of the blockage 51. This may be particularly advantageous in the event that plaque 56 is covering a portion of the wall 55 of the vessel.

Figure 7:
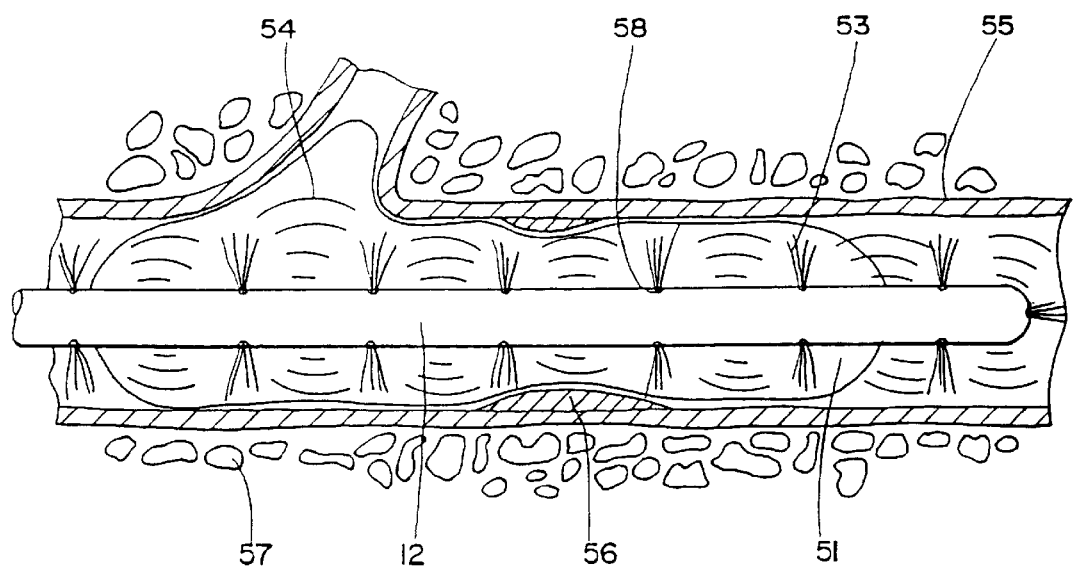
FIG. 7 is a schematic perspective view of the preferred embodiment of the present invention shown in FIG. 5 wherein the distal treatment tip of the catheter protrudes through the clot/obstruction and the lysing agent sprays inside the clot and both proximal and distal to the clot.

As shown in FIG. 7, it is also possible to have a plurality of holes 58 dispensing the lysing agent 53, both distal to the obstruction 51 and interior to the obstruction. Such a combination of vibrational motion and spraying of lysing agent into the blockage facilitates the rapid disruption of the blockage 51.

Figure 8:
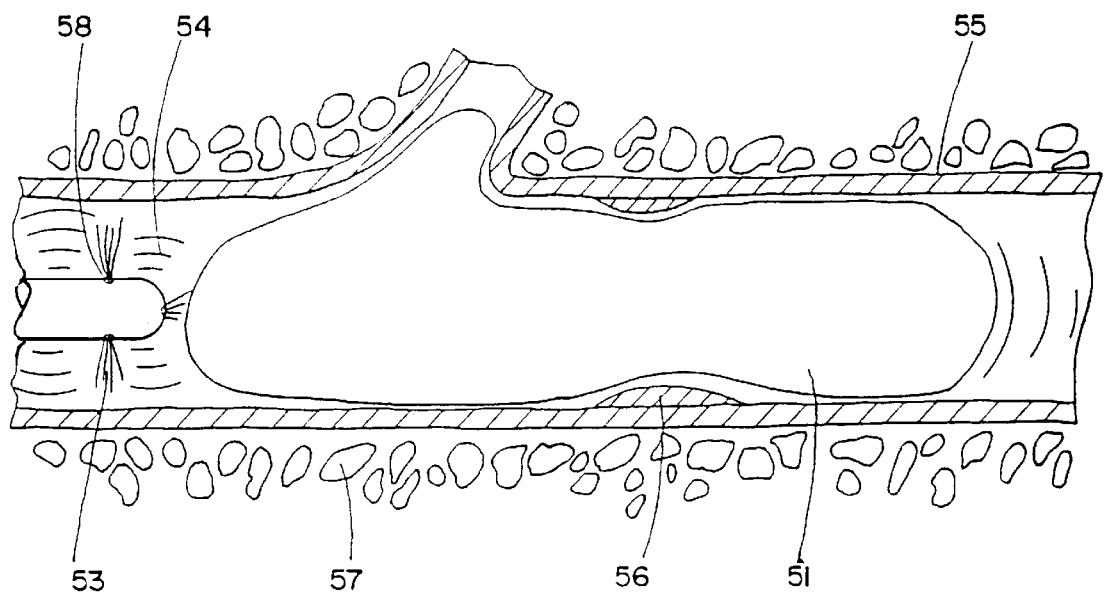
FIG. 8 is a cross-sectional view of the preferred embodiment of the present invention in FIG. 5 wherein the distal treatment tip of the motion catheter is located proximal to the obstruction and the spraying lysing agent delivered from the tip in a direction parallel to the long axis of the catheter.

In FIG. 8, the distal tip 12 is advanced until it is in juxtaposition with the proximal end of the blockage 51. When the distal tip is in position, the vibrational waves 54 in combination with the release or spraying of lysing agent 53 affect the dissolution of the blockage 51.

Figure 9:
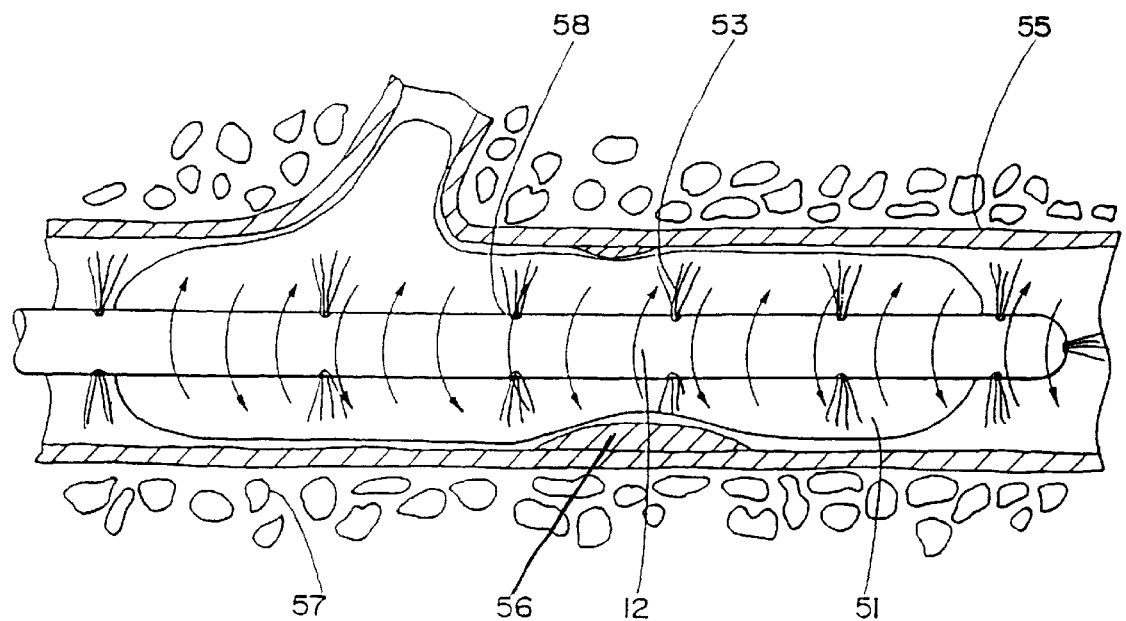
FIG. 9 is a perspective view of the distal tip of the preferred embodiment of the present invention shown in FIG. 5 wherein the motion catheter is rotating or oscillating in a to-and-fro motion while the lysing agent is being dispensed.

Up until now, we've been referring primarily to vibrational motion in the tip of the catheter that is axial oscillatory motion generally in the direction of the axis of the catheter. FIG. 9 shows a rotary motion which may be imparted to the tip of the catheter by applying an oscillating rotary motion to the proximal end of the catheter. The arrows in FIG. 9 show the rotation of various elements of the tip of the catheter with respect to adjacent elements of the catheter. The catheter 10 is a flexible structure and these rotational waves can travel down the catheter changing direction. Such rotary motion, particularly when the tip 12 is embedded within the blockage 51, may be particularly advantageous for facilitating the penetration of lysing agent 53 sprayed from the holes 58 in the distal tip 12 of the catheter 10. The rotational arrows are generally indicated at 58.

Figure 10:
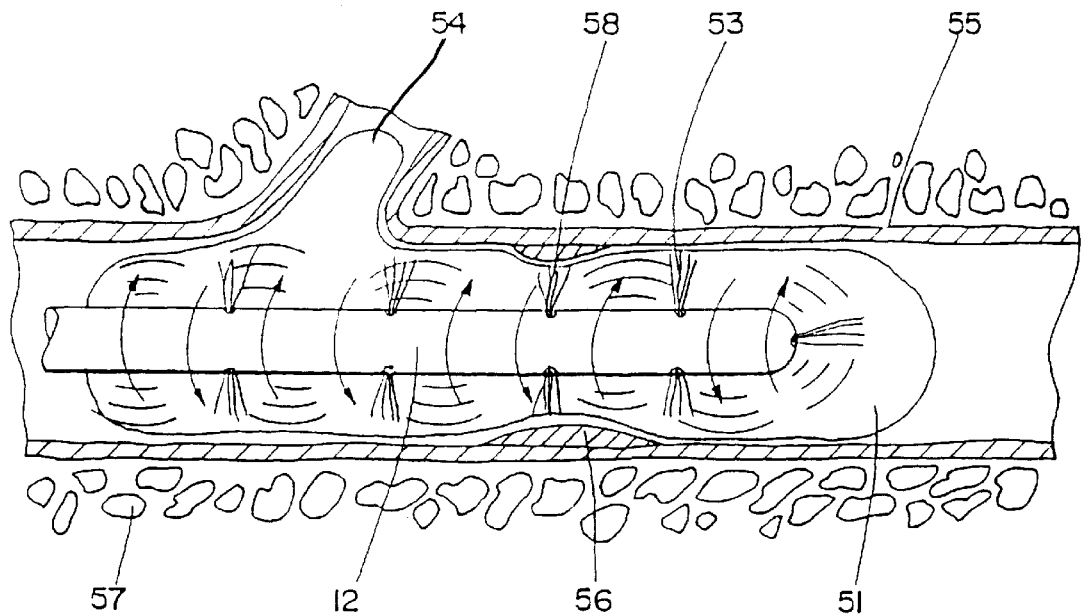
FIG. 10 is a cross-sectional view of the preferred embodiment of the present invention shown in FIG. 5 wherein the lysing agent is dispensed by holes in the distal tip and is directed within and/or under the body of the obstruction.

FIG. 10 shows a translational motion which can be used in combination with the rotary motion of FIG. 9, which combination of motions may cause the tip 12 of the catheter 10 to "wobble" or "wiggle" causing mixing and enabling the lysing agent 53 to more rapidly permeate the obstruction 51 facilitating dissolution thereof.

Figure 11:
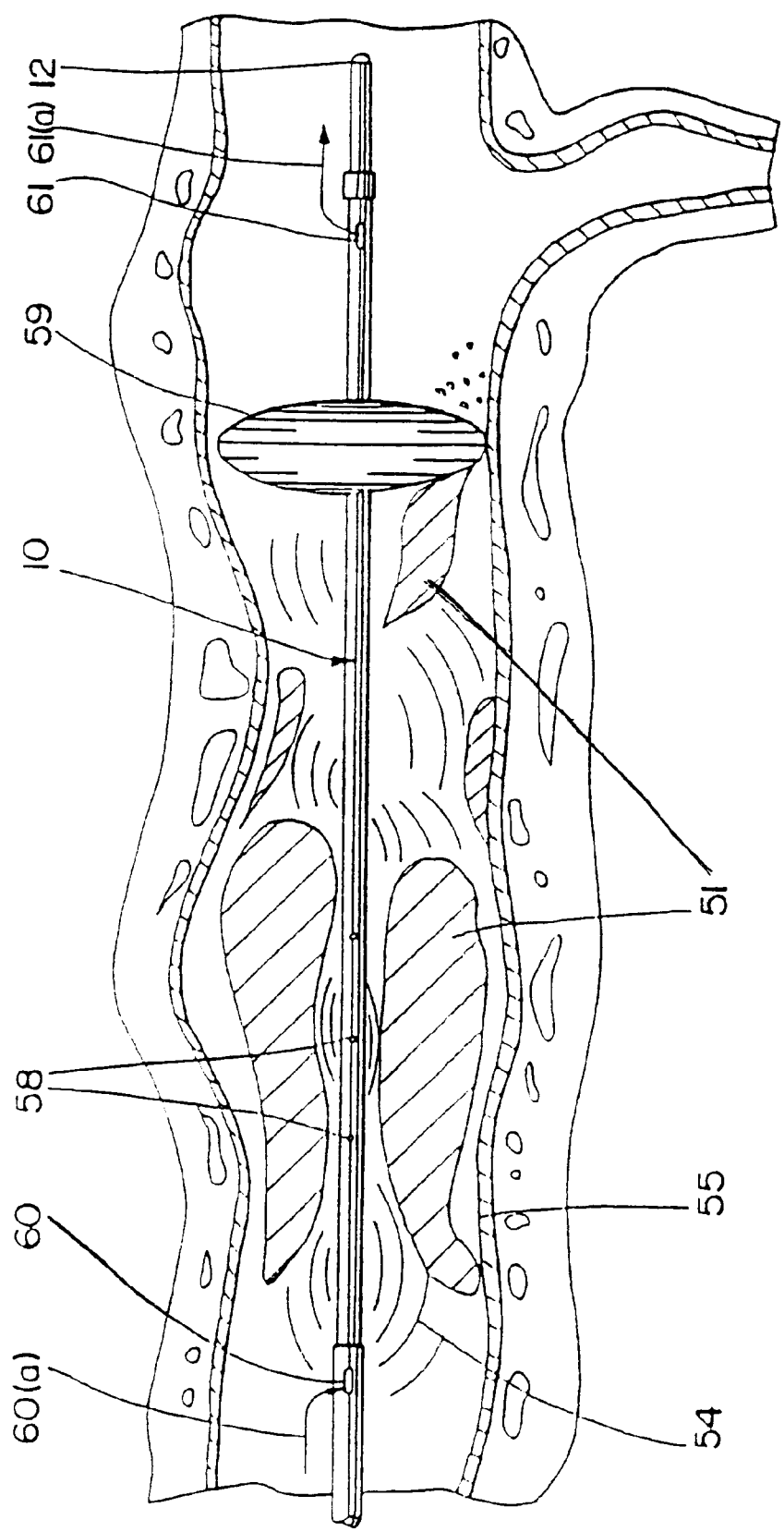
FIG. 11 is a cross-sectional view of a second preferred embodiment of the present invention wherein an inflatable vessel occluder near the distal tip of the catheter blocks the flow of blood around the outside of the catheter thereby forcing the blood to flow through a particle filter housed within a perfusion channel within the catheter.

During the dissolution process, fragments of the obstructing thrombus may break loose and obstruct the vascular system at one or more points remote from the original obstruction. A second preferred embodiment of the catheter of the present invention which is especially designed to prevent the dissemination of such fragments to other points in the vascular system is shown in FIG. 11. In this second preferred embodiment the catheter 10 has a coaxial inflatable member 59 on the outer surface thereof between the holes 58, through which holes lysing agent (not shown) is sprayed, and the distal tip 12 of the catheter 10. A perfusion channel (not shown) housed within the body portion of the catheter 10 is coextensive with the portion of the catheter between fenestrations 60 and 61 in the outer wall of the catheter 10 providing fluid communication therebetween. Blood enters the perfusion channel (not shown) through the proximal fenestration 60 in the direction indicated by arrow 60(a). Any fragments of thrombus entrained in the blood as the blood enters the proximal fenestration 60 will pass into the catheter perfusion channel. A particle filter (not shown) is deployed within the perfusion channel to remove such fragments before the blood exits the perfusion channel through the distal fenestration 61 as indicated by arrow 61(a). The filter (not shown) is in-line with the perfusion channel connecting fenestrations 60 and 61 and can be a polymeric or metallic mesh or "birds nest" or a filter of the type used to remove fat cells from an aspirate described in U.S. Pat. No. 4,834,703 to Dubrul, et al., (incorporated herein by reference). Such a filter must be in-line with the perfusion channel and coextensive with at least a portion thereof to effectively remove fragments of thrombus and any other unwanted particulate debris from the perftisate 60(a) and 61(a).

EXAMPLE

To prove evaluate the effectiveness of the present invention, an in vitro experiment was performed to evaluate the advantage, if any, of using the motion catheter to disperse clots rather than existing technology. Blood clots were created in a test tube. The weight of each clot was measured prior to experimentation. The clots were then treated with urokinase at a rate of 5000 IU/ml for 5 minutes to a total of 15,000 IU. The clot (thrombus) weights were measured initially and finally to determine the amount of lysing that had taken place. One of the groups (Group 1) was used as a control. Nothing was done to the Group 1 thrombi except initial and final weighing. Another group (Group 2) was treated with the same amount of lysing agent, but the lysing agent was dispersed through the motion catheter while the catheter was being very slowly vibrated, the catheter was placed proximal to the clot in similar fashion as was the aforementioned group. In Group 3, the motion catheter was placed in the clot as in Groups 1 and 2, but the urokinase was pulsed into the clot and no motion was applied to the system. In Group 4, the lysing agent was pulsed into the clot as in Group 3, but a slow (low frequency) vibratory motion was applied to the motion catheter. Group 5 clots were treated with saline and slow vibration. In Groups 2, 4, and 5 (Groups with a motion applied to the motion cateheter) the amount of lysing of the clot/thrombus was greatly increased as determined by the difference in weight of the clot/thrombus before and after the one hour treatment. Those results are tabulated in Table 1 where the percentage of lysing is the difference between the initial and final weight of the clots divided by the initial weight, the quotient multiplied ×100.

TABLE 1

| Group 1 | 4.5% Lysing |
|---|---|
| Group 2 | 68% |
| Group 3 | 26% |
| Group 4 | 45% |
| Group 5 | 45% |

From the foregoing data it is clear that low frequency vibration with administration of a lysing agent (Group 2) gives the best results. Surprisingly, the Group 5 clots (no lysing agent) that were subjected only to a low frequency (1–1000 Hz) vibrating member in the presence of saline exhibited substantial dissolution under the conditions of the experiment. This suggests that the introduction of a simple intravascular wire or similar elongate member vibrating at lower frequencies (<1000 Hz) into a blocked vessel may be useful for disrupting clots.

The invention will now be described with respect to FIGS. 12 through 15. An aspiration device generally indicated by the numeral 100, is shown with respect to FIG. 12. The aspiration device 100 includes a suction mechanism 102 located at the proximal end 11 of the motion catheter 10. The aspiration device 100 additionally includes an outer sleeve 104, as shown more clearly in FIG. 13. The outer sleeve extends from the proximal end 11 to the distal end 12 of the device 10.

During, after, or before the obliteration of the atheroma or other obstruction in the blood vessel, small particles represented by fragments 106 exist within the blood vessel. As is well known, these fragments can cause extreme health difficulties such as stroke, ischemia, collateral vessel blockage and the like. It is thus, advantageous to remove such particles 106 from the blood vessel. The aspiration device 100, when activated, causes a suctioning, or low pressure, to be developed at the proximal end drawing blood in a direction of the arrows 108. The aspiration device is activated by the suction mechanism 102. The suction mechanism 102 includes a chamber 110 and a plunger 112. When the plunger 112 is pulled away from the chamber 110, a low pressure area or vacuum is created in a lumen of the catheter 10. As noted below, this causes the blood flow to proceed from the distal end to the proximal end. Other vacuum sources such as a mechanical pump, or an electromechanical pump, may also be used as the suctioning mechanism 102, to create the low pressure area.

Figure 12:
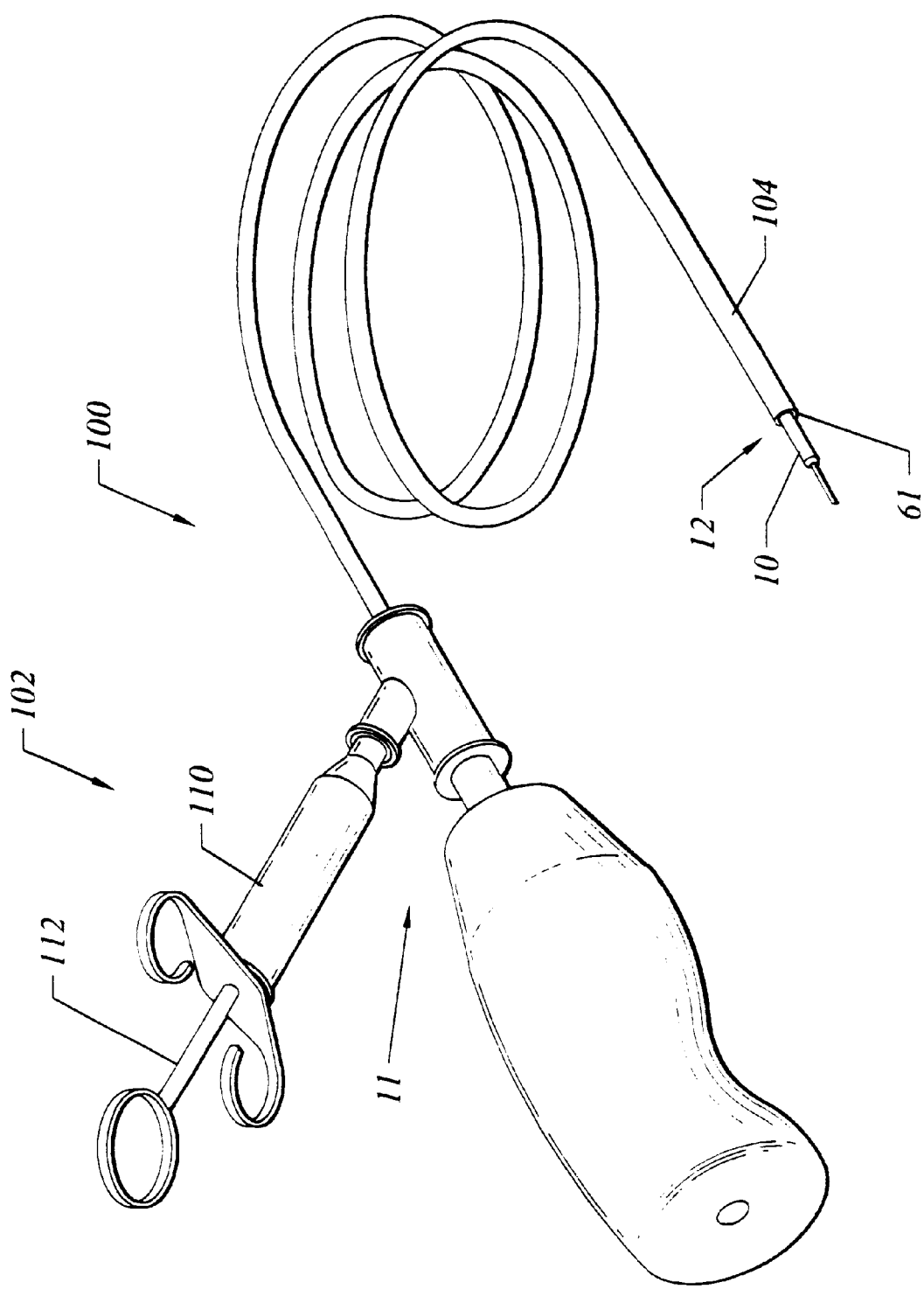
FIG. 12 illustrates a prospective view of an aspiration embodiment of the present invention.

It will also be appreciated that, while it is not shown in FIG. 12, a third port could be added comprising an injection port. The injection port, while not shown here, is shown in the earlier filed drawings connected with this matter, specifically FIGS. 1 of U.S. Pat. Nos. 5,498,236 and 5,380,273. Additionally, the motion catheter 10 may include distal end 12 having an infusion port such as infusion port 61, as described with reference to FIG. 11 of the above identified patents.

It will be appreciated that the injection port and the aspiration port may be activated independently and simultaneously. Thus, while fluid may be moved up and through the catheter from the distal end to the proximal end, it may also be appreciated that fluid may also be moved down and through the proximal end 11 through the distal end 12 using the injection port. In this way, while simultaneously aspirating, a fluid such as a medicament, for example saline or sterile water, may be injected into the patient's blood vessel simultaneously with the aspiration process. Additionally, it will be appreciated that fluid of any kind can be moved in either direction through the catheter using aspiration and infusion including fluid such as a contrast fluid.

It will be appreciated that FIG. 11 of the above identified patents, noted particularly at U.S. Pat. No. 5,498,236, col. 6, lines 50 through 57, and at col. 6, line 65 through col. 7, line 12 and U.S. Pat. No. 5,380,273, col. 6, line 58 through col. 7, line 25, specifically disclose polymeric, metallic mesh, or birds nest filter described with respect to aspiration and the like. A filter such as the one described above, or filter cartridge as specifically referred to in U.S. Pat. No. 4,834,703, may be inserted within the outer sleeve 104 coaxially with the catheter. The filter cartridge, or filter, traps the particulate matter or particles 106, thereby removing the same from the blood vessel and consequently from the blood stream.

Figure 13:
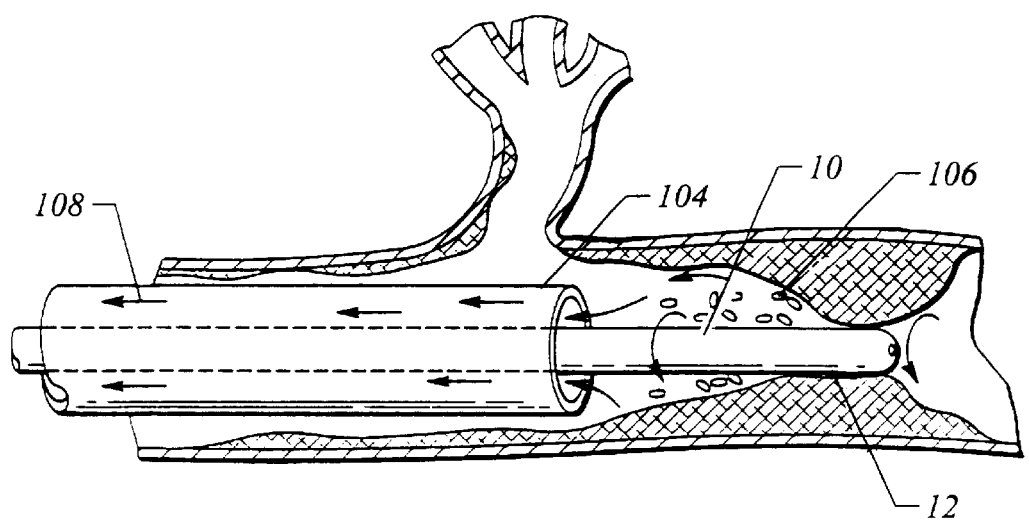
FIG. 13 illustrates the distal end of an aspiration embodiment of the present invention.

As shown in FIGS. 12 and 13, the motion catheter 10 may be activated during aspiration. It may be desirable to remove particulate matter 106 as the tip is in motion to either vibration or rotation. Alternatively, the aspiration device 100 may be activated both after and before activation of the motion catheter.

Figure 14:
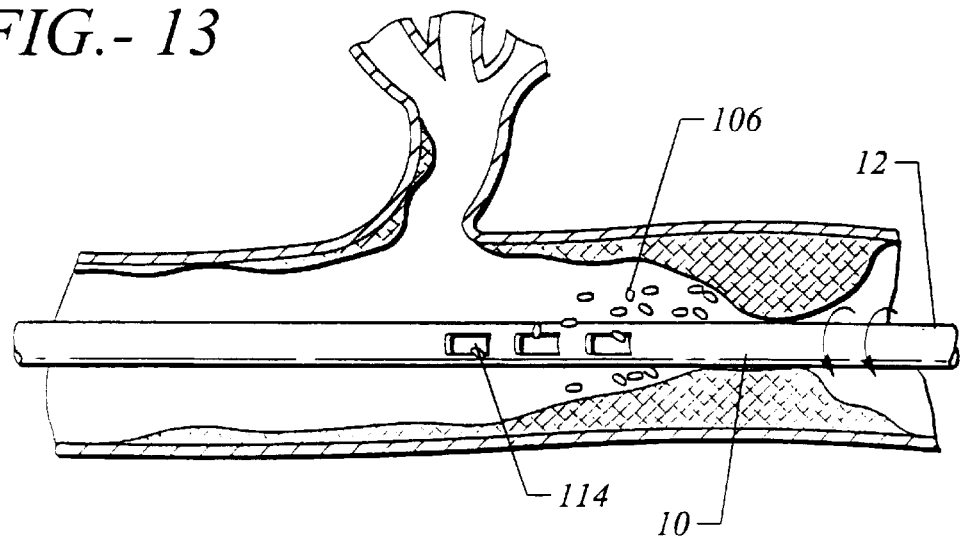
FIG. 14 illustrates an alternate embodiment of an aspiration device of the present invention.

With respect to FIG. 14, there is shown another embodiment of the aspiration device 100, wherein the distal end 12 of the motion catheter 10 includes the distal end having fenestrations. In this embodiment, the in-line polymeric filter and/or filter cartridge would be inserted within the motion catheter itself to trap the particulate matter 106. The fenestrations 114 are shown in FIG. 14 as being generally rectangular in shape. It will be appreciated that a variety of shapes, sizes, and styles may be appropriate depending upon the particular function, blood flow, and level of force of the aspiration device 100. Similarly to the previously discussed embodiment shown in FIG. 13, the embodiment shown in FIG. 14 having fenestrations 114, allow the particulate matter to enter the fenestrations as a result of the low pressure being created by the activation of the aspiration device 100, and thereby removed by the blood stream through the in-line polymeric filters as discussed above.

Figure 15:
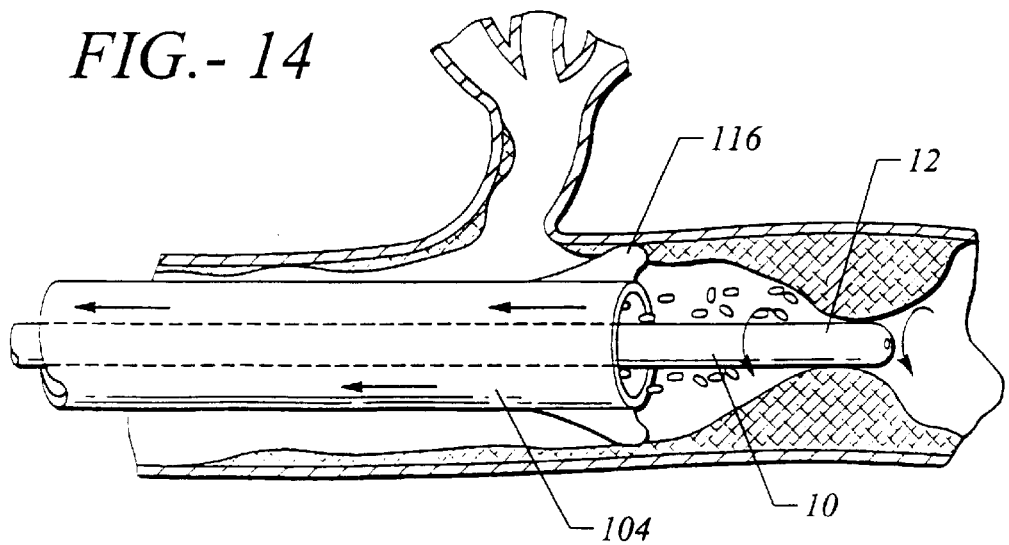
FIG. 15 illustrates an additional alternative embodiment of an aspiration device of the present invention.

With respect to FIG. 15, there is shown a third embodiment of the aspiration device 100 in accordance with this invention. In the aspiration device of FIG. 15, the outer sleeve 104 includes an occluding mechanism 116 which prevents blood from preceding around the occluding mechanism 116 and causes blood flow to enter the proximal end of the outer sleeve 104. Similar to the previously discussed embodiments of FIGS. 13 and 14, the occluding mechanism 116 operates to force blood flow to an area where an in-line polymeric filter or filter cartridge may trap the particulate matter 106, thereby removing it from the blood vessel and consequently the blood stream.

It will be appreciated that a variety of other filters not described herein may be used. For example, the filters may comprise a variety of different shapes and sizes and may be located in slightly different positions on the catheter.

The occluding mechanism 116 comprises an exemplary embodiment, an angioplasty type balloon which is selectively inflated to cause a blockage in the blood vessel as shown clearly in FIG. 15. Other occluding mechanisms of course are within the scope and spirit of this invention.

Also, it will be appreciated that an occlusion balloon, or centering balloon, may also be used in place of the angioplasty type balloon. The occlusion or centering balloon is distinguished from the angioplasty balloon because it does not inflate to a predetermined sized. Rather the occlusion balloon continues to increase in size the more it is inflated. Also, the occlusion balloon conforms itself to the shape and size of the inner vessel wall. In some instances, it may well be preferable to use the occlusion balloon as opposed to the angioplasty type balloon. It will be understood herein that when referring to the angioplasty balloon below, that other types of balloons including the occlusion or centering balloon, may well be substituted in its place.

Similarly with respect to FIGS. 13 and 14, the aspiration device of FIG. 15 may be used before, after, or during activation of the motion catheter 10.

Figure 16:
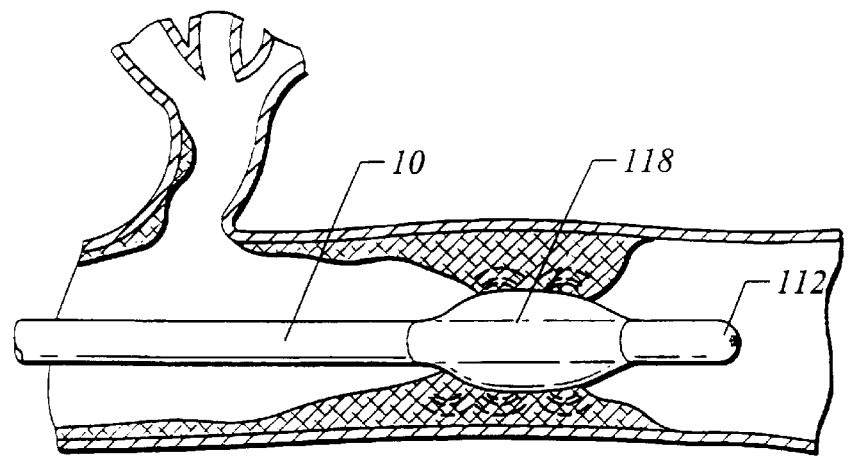
FIG. 16 illustrates the use of a balloon mechanism with the catheter of the present invention.

With respect to FIG. 16, there is shown another embodiment of the motion catheter 10 in accordance with this invention. In this embodiment, the motion catheter 10 includes an angioplasty-type balloon 118 at the distal end 12. The angioplasty-type balloon 118 is formed, as is conventional in the field and more particularly as shown and described in U.S. Pat. Nos. 4,922,905, 4,838,268, 4,808,164, and 4,707,670, which are specifically incorporated herein by reference, and represents a typical angioplasty-type balloon. As noted above, an occlusion balloon such as those identified in U.S. Pat. Nos. 5,637,086, 5,222,970, 5,074,869, and 4,130,119, which are also specifically incorporated herein by reference, may be substituted for the angioplasty-type balloon.

In the embodiment shown in FIG. 16 showing the angioplasty balloon 118, the motion catheter may be activated before, during, or after, balloon expansion. It is believed that such motion of the angioplasty balloon is particularly useful in relieving the blood vessel obstruction. It will be appreciated that the various elements, shown in FIGS. 12 through 15, may be combined or used alternatively with the embodiment shown in FIG. 16 within the spirit and scope of this invention. However, it is not necessary for the beneficial effects and advantages of the embodiment shown in FIG. 16 to provide the alternative structures shown and described in such combinations.

With respect to FIGS. 17 through 20, there is shown an alternate embodiment of the motion catheter device 10 having a coaxially filter trap 120. As similarly shown with respect to the '273 and '236 patents described above, the filter trap 120 is deployable and expandable as shown in FIGS. 17 through 20.

Figure 17:
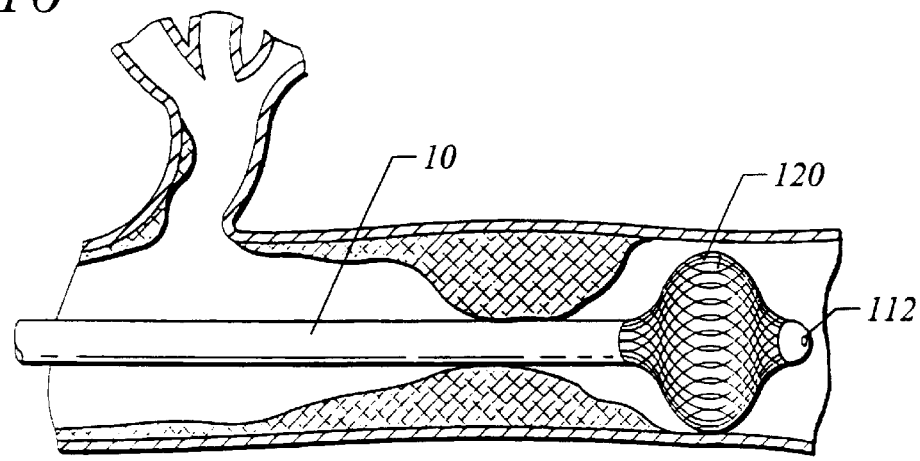
FIGS. 17 through 20 illustrate various embodiments of a filter trap with and without the use of the aspiration device of the present invention.
Figure 18:
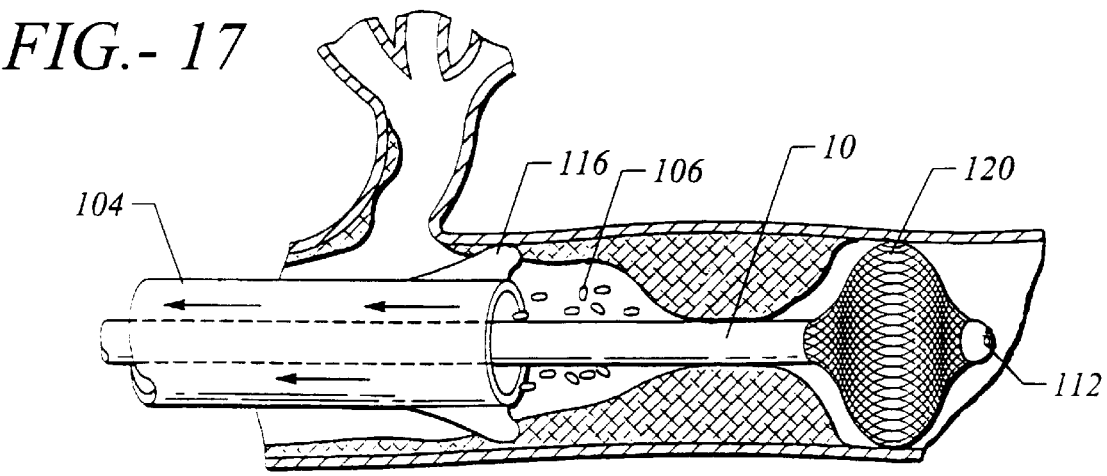
Figure 19:
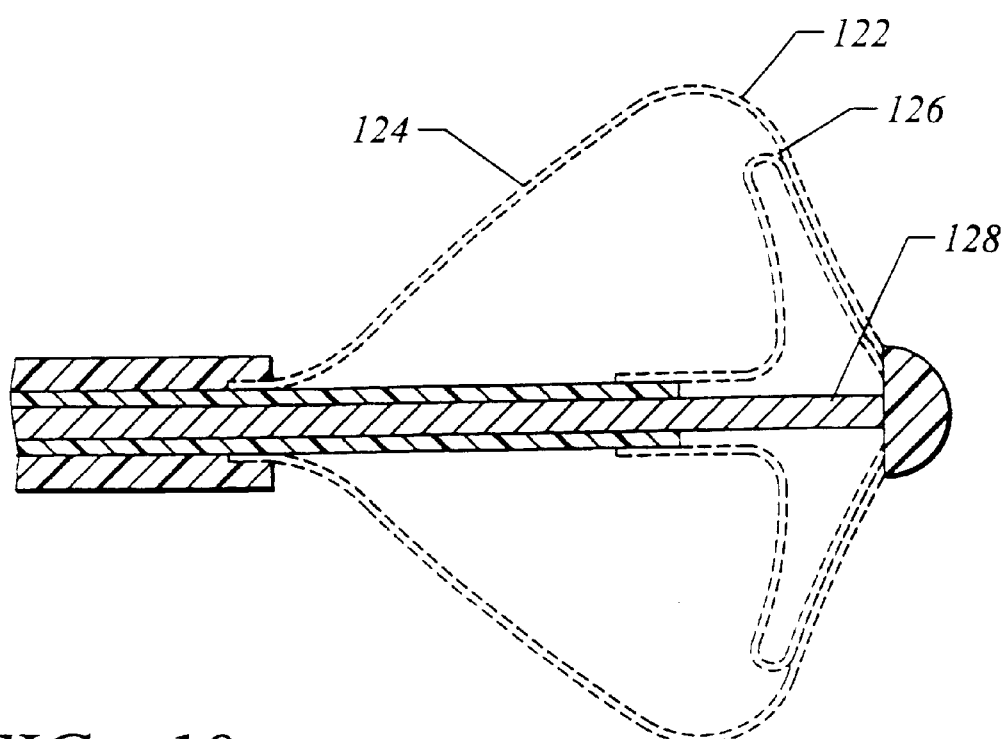
Figure 20:
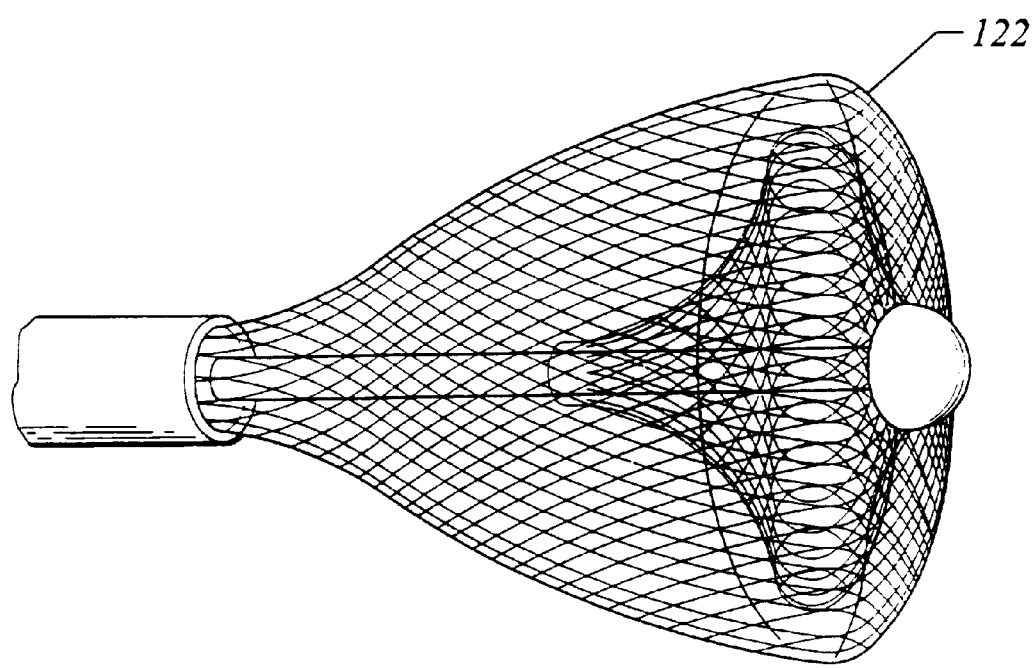

In FIG. 17 the filter trap is in its initial stage of deployment. In FIG. 18 the filter trap has been fully expanded. Additionally, in FIG. 18 there is shown the filter trap 120 used in combination with the occluding mechanism 116. Using a combination of these devices provides the invention with the ability to trap particulate matter 106, whether it flowed against or with the arrows 108. It will be readily appreciated that any particulate matter traveling in the direction opposite of the arrows would be trapped within the filter trap 120. The filter trap 120 is made of polymeric mesh and can be expanded to a variety of shapes and sizes. The device 10 (not shown) includes activation mechanism (not shown) which can readily expand or contract the filter trap 120.

It will be appreciated that the inflatable coaxial structure described with respect to the '273 and '236 patents can, in fact, define a filter such as the ones described above. It will also be appreciated that a combination of the inventions taught by the '236 and '273 patents and the disclosure herein can be combined. In fact, an occluding element could be distal to the distal end of the catheter 12 with a filter being in-line in an aspiration device. In this way, the particulate matter is prevented from flowing down stream by the occlusion mechanism while the aspiration device is activated causing the particulate matter to be drawn back into the inflatable coaxial filters. Thus, the fluid down stream of the occluding mechanism would be relatively free of particulate matter while the particulate matter would be substantially trapped within the coaxial filter.

Upon activation of the motion catheter, a spinning vortex is created. Upon the direction of the user, the particulate matter 106 can be directed, either proximally or distally, to be trapped by the filter system described above. Again, the object of trapping particulate matter is accomplished. In this way, the spinning vortex causes additional and further particulate matter to be trapped in a coaxial filter.

Additionally, polymeric shapes such as a frusto-conical shape filter trap alternative embodiment generally indicated by the numeral 122, may alternatively be employed. The filter trap 122, shown in cross section FIG. 19, includes an outer member 124 and an inner member 126. Both members are connected to a shaft 128. Upon activation both inner and outer members, 124 and 126 respectively, are deployed or expanded within the blood vessel. Upon deactivation, both members are contracted and fit snugly along shaft 128. The dual filter has the purpose of (1) sealing against the vessel wall, (2) capturing large and small particles and the prevention of dissemination of such fragments, (3) the centering of the catheter during motion, (4) capturing and holding particulate matter for dissolution, and (5) capturing of particulate matter allowing blood or smaller particles to flow through, whereby, at the end of the procedure, the filter trap is un-deployed and particulate matter is removed.

The filter shaft system, upon trapping the particulate matter 106, can either remain deployed until the blood flow causes the particulate matter 106 to be dissolved or can be contracted and then removing the device 10 from the blood vessel and then removing the trapped particulate matter 106 will thus remove the particular matter from the blood system.

The aforesaid specification taken in connection with the drawings and the aforementioned experiment sets forth the preferred embodiments of the present invention. The embodiments of the invention disclosed herein are the best modes contemplated by the inventors for carrying out their invention in a commercial environment, although it should be understood that various modification can be accomplished within the scope of the invention.

What is claimed is:

1. A device for insertion into a body lumen useful for dissolution of obstructive material, the device comprising:
    a source of low-frequency mechanical motion;
    an elongate member having a proximal portion, a distal portion, and an outer surface, and a longitudinal axis therebetween, wherein the proximal portion is matingly engageable with the source of mechanical motion; and
    an expandable member disposed on said elongate member distal portion.

2. A device of claim 1, further comprising a sleeve disposed coaxially over the elongate member, said sleeve having an inner surface and an outer surface such that the coaxial combination of said elongate member and said sleeve forms an annular space between said elongate member outer surface and said sleeve inner surface, wherein said expandable member is a balloon mounted on the sleeve.

3. A device of claim 2, wherein said device further includes a second expandable member disposed on said sleeve adjacent said elongate member proximal portion.

4. A device of claim 3, wherein said second expandable member is a balloon.

5. A device of claim 3, wherein said second expandable member is a filter.

6. A device of claim 1, wherein said expandable member is a filter trap.

7. A device of claim 2, further comprising a means for aspirating, wherein said annular space is in fluid communication with the means for aspirating.

8. A device of claim 1, wherein said elongate member has a lumen disposed between said elongate member distal end and said elongate member proximal end.

9. A device of claim 8, wherein said lumen is in fluid communication with an inlet port on the proximal end of the elongate member and an outlet port on the distal end of the elongate member which is distal of said expandable member, wherein a filter element is disposed in said lumen.

10. A device of claim 1, wherein said source of mechanical motion provides rotational and/or translational motion.

11. A device for insertion into a body lumen useful for dissolution of obstructive material, the device comprising:
    a source of low-frequency mechanical motion;
    an elongate member having a proximal portion, a distal portion, an outer surface, and a longitudinal axis therebetween, wherein the proximal portion is matingly engageable with the source of mechanical motion;
    a sleeve disposed coaxially over the elongate member, said sleeve having an inner surface and an outer surface such that the coaxial combination of said elongate member and said sleeve forms an annular space between said elongate member outer surface and said sleeve inner surface; and
    an expandable member disposed on said sleeve adjacent said elongate member distal portion.

12. A device of claim 11, wherein said expandable member is a balloon.

13. A device of claim 12, wherein said device further includes a second expandable member disposed on said sleeve adjacent said elongate member proximal portion.

14. A device of claim 13, wherein said second expandable member is a balloon.

15. A device of claim 13, wherein said second expandable member is a filter.

16. A device of claim 11, wherein said expandable member is a filter trap.

17. A device of claim 11, further comprising a means for aspirating, wherein said annular space is in fluid communication with the means for aspirating.

18. A device of claim 11, wherein said source of mechanical motion provides rotational and/or translational motion.

19. A device for insertion into a body lumen useful for dissolution of obstructive material, the device comprising:
    a source of low-frequency mechanical motion;
    an elongate member having a proximal portion, a distal portion, an outer surface, and a longitudinal axis therebetween, wherein the proximal portion is matingly engageable with the source of mechanical motion;
    a sleeve disposed coaxially around said elongate member, said sleeve having an inner surface and an outer surface, such that said inner surface of said sleeve and said outer surface of said elongate member form an annular space; and
    a mechanism for aspirating any dissolved obstructed material through said annular space for removal from said body lumen.

20. A device of claim 19, further comprising an expandable member disposed on said sleeve adjacent said elongate member distal portion.

21. A device of claim 20, wherein said expandable member is a balloon.

22. A device of claim 20, wherein said expandable member is a filter.

23. A device of claim 20, further comprising a second expandable member disposed on said sleeve adjacent said elongate member proximal portion.

24. A device of claim 23, wherein said second expandable member is a balloon.

25. A device of claim 23, wherein said second expandable member is a filter.

26. A device of claim 19, wherein said source of mechanical motion provides rotational and/or translational motion.

27. A device for insertion into a body lumen useful for dissolution of obstructive material, the device comprising:

a source of low-frequency mechanical motion;

an elongate member having a proximal portion, a distal portion and a longitudinal axis therebetween, and further comprising an outer surface and an inner lumen extending between said distal portion and said proximal portion, wherein said proximal portion is matingly engageable with the source of mechanical motion; and said elongate member including one or more fenestrations located along the said elongated member longitudinal axis and in fluid communication between said elongate member outer surface and said elongate member inner lumen.

28. A device of claim 27, further comprising means for aspirating fluid from within said body lumen, through said fenestrations to a location outside said body lumen.

29. A device of claim 27, her comprising an expandable member located on said elongate member distal portion.

30. A device of claim 29, wherein said expandable member is a filter trap.

31. A device of claims 29, wherein said expandable member is a balloon.

32. A device of claim 27, further comprising a second expandable member located on said elongate member proximal portion.

33. A device of claim 32, wherein said second expandable member is balloon.

34. A device of claim 32, wherein said expandable member is a filter trap.

35. A device of claim 27, wherein said source of mechanical motion provides rotational and/or translational motion.

36. A device for insertion into a body lumen useful for dissolution of obstructive material, the device comprising:

a source of low-frequency mechanical motion;

a unitary elongate member having a proximal portion, a distal portion, and an outer surface, and a longitudinal axis therebetween, wherein the proximal portion is matingly engageable with the source of mechanical motion; and a sleeve disposed coaxially over the elongate member, said sleeve having an inner surface and an outer surface such that the coaxial combination of said elongate member and said sleeve forms an annular space between said elongate member outer surface and said sleeve inner surface.

37. A device of claim 36, further comprising an expandable member disposed on said sleeve adjacent said elongate member distal portion.

38. A device of claim 37, wherein said expandable member is a balloon.

39. A device of claim 37, wherein said device further includes a second expandable member disposed on said sleeve adjacent said elongate member proximal portion.

40. A device of claim 39, wherein said second expandable member is a balloon.

41. A device of claim 39, wherein said second expandable member is a filter.

42. A device of claim 39, wherein said second expandable is a filter trap.

43. A device of claim 36, further comprising a means for aspirating, wherein said annular space is in fluid communication with the means for aspirating.

44. A device of claim 36, wherein said elongate member has a lumen disposed between said elongate member distal end and said elongate member proximal end.

45. A device of claim 44, wherein said lumen is in fluid communication with an inlet port on the end of the elongate member and an outlet port on the distal end of the elongate member which is distal of said expandable member, wherein a filter element is disposed in said lumen.

46. A device of claim 36, wherein said source of mechanical motion provides rotational and/or translational motion.

* * * * *